United States Patent
Kadokura et al.

(10) Patent No.: US 6,376,692 B1
(45) Date of Patent: Apr. 23, 2002

(54) ZIRCONIUM ALKOXYTRIS (β-DIKETONATE), PROCESS FOR MANUFACTURING THE SAME, AND LIQUID COMPOSITION FOR FORMATION OF PZT FILM

(75) Inventors: Hidekimi Kadokura, Tokyo; Yumie Okuhara, Sakado, both of (JP)

(73) Assignee: Kabushikikaisha Kojundokagaku Kenkyusho, Tokyo (JP)

( * ) Notice: Subject to any disclaimer, the term of this patent is extended or adjusted under 35 U.S.C. 154(b) by 0 days.

(21) Appl. No.: 09/680,364

(22) Filed: Oct. 5, 2000

(30) Foreign Application Priority Data

Nov. 19, 1999 (JP) .............................. 11-370762

(51) Int. Cl.⁷ .............................. C07F 7/00; C23C 16/40
(52) U.S. Cl. ..................... 556/40; 106/287.19
(58) Field of Search ..................... 556/40; 106/287.19

(56) References Cited

PUBLICATIONS

Saxena et al., J. Chem. Soc. (A), vol. 6, pp. 904–907 (1970).*

* cited by examiner

Primary Examiner—Porfirio Nazario-Gonzalez
(74) Attorney, Agent, or Firm—Fattibene & Fattibene; Paul A. Fattibene; Arthur T. Fattibene

(57) ABSTRACT

There is provided a compound for the formation of a PZT film using $Pb(dpm)_2$ where the compound has a low reactivity with $Pb(dpm)_2$, has a thermal decomposition temperature which is lower than $Zr(dpm)_4$ and is well soluble in a solvent such as butyl acetate and toluene. There is also provided a process for the manufacture of the compound. There is further provided a liquid composition for the formation of a PZT film using the compound. The novel compound $Zr(OiPr)(dpm)_3$ has a sublimation pressure of 0.1 Torr/160° C. and is able to form a $ZrO_2$ film by a CVD at 400° C. That can be prepared by the reaction of 1 mol of $Zr(OiPr)_4$ and 3 mol of dpmH in an organic solvent followed by purifying by sublimation. A solution of $Pb(dpm)_2$, $Zr(OiPr)(dpm)_3$ and $Ti(OiPr)_2(dpm)_2$ dissolved in butyl acetate has a long pot life and forms a PZT film by a solution flash CVD method.

5 Claims, 4 Drawing Sheets

ZIRCONIUM ALKOXYTRIS (β-DIKETONATE), PROCESS FOR MANUFACTURING THE SAME, AND LIQUID COMPOSITION FOR FORMATION OF PZT FILM

BACKGROUND OF THE INVENTION

1. Field of the Invention

The present invention relates to a Zr compound which is suitable as a material for the formation of a Zr-containing metal oxide film useful as a ferroelectric film, optical thin film, catalytic thin film, solid electrolyte thin film, etc. by a chemical vapor deposition method (CVD method), to a process for manufacturing the same and to a liquid composition for the formation of a PZT film.

2. Description of the Prior Art

Considerations have been carried out for the formation of a PZT film which is a ferroelectric substance for nonvolatile memory by a CVD method. It has been also desired that the temperature for the formation of the film is as low as possible. Method for supplying the material in the CVD method is roughly classified into two. One is a method A where the pure material compound is introduced into a CVD chamber as it is or after carried with an inert carrier gas and another is a method B where the material compound is dissolved in an organic solvent and the solution is flash-evaporated and introduced into the CVD chamber. In any of those methods, there is a possibility that, before the mixed gas arrives the substrate, the components thereof react each other to lower the volatility or that a ligand exchange occurs to change the property. It is desirable that such a thing is avoided and also that decomposition characteristics of the compounds of Pb, Ti and Zr such as thermal decomposition temperature are similar. In the method B, the three components, i.e. Pb, Zr and Ti, are made into a single solution as an ultimate method but, in that case, it is requested that neither reaction nor deterioration takes place in the solution until being subjected to a CVD process.

With regard to a Pb material for the manufacture of a PZT film by the CVD method, that of a PbEt$_4$ type and a Pb(dpm)$_2$ type are available but, since the PbEt$_4$ type is highly toxic, the Pb(dpm)$_2$ type having weak toxicity is appropriate for a large-scale production. There has been a demand for Zr compound and Ti compound which are not reactive with Pb(dpm)$_2$ and have similar thermal decomposition characteristics thereto. In the method B, an interaction with a solvent and a solubility are important factors as well.

With regard to the method A, Tatsumi, et al. disclosed in Extended Abstracts (59$^{th}$ Autumn Meet. 1998); Japan Society of Applied Physics, page 447 that crystallization at the temperature of as low as 430° C. occurred by an extremely low-pressure CVD by supplying pure Pb(dpm)$_2$-Zr(OtBu)$_4$-Ti(OiPr)$_4$ at its own pressure.

With regard to the method B, there is a disclosure in Japanese Patent Laid-Open No. 298762/1998 that film is formed by a CVD method from a combination of Pb dipivaloylmethanate-Zr dipivaloylmethanate-Ti dipivaloyl-methanate (Pb:Zr:Ti=2.2:1:1) using THF as a solvent. Although no chemical formula is given for the Zr dipivaloylmethanate, it is presumed to be Zr(dpm)$_4$ which was available at that time.

In claim 15, U.S. Pat. No. 5,820,664 (October 1998) discloses a solution of Pb(dpm)$_2$-Zr(dpm)$_4$-Ti(OiPr)$_2$(dpm)$_2$ in a mixed solvent of 45% to 88% of THF, 10% to 35% of isopropanol and 2% to 20% of tetraglyme.

P. C. Van Buskirk, et al. mentions in *Integrated Ferroelectrics*, Vol. 21, 273 (1998) that Pb(dpm)$_2$-Zr(dpm)$_4$-Ti(OiPr)$_2$(dpm)$_2$ will be the mainstream combination in future.

WO 98/51837 (November, 1998) discloses that, since thermal decomposition point of Zr(dpm)$_4$ is considerably higher than that of Pb(dpm)$_2$, the use of novel compounds which are Zr(OiPr)$_2$(dpm)$_2$ and Zr$_2$(OiPr)$_6$(dpm)$_2$ instead of Zr(dpm)$_4$ is preferred because they are apt to be decomposed at low temperature. The compounds claimed by the patent is Zr$_x$(OR)$_y$L$_z$(in which R is an alkyl group; L is a β-diketonate; x is 1 or 2; y is 2, 4 or 6; and z is 1 or 2). In the patent and also in an article by the inventor of the patent (*Inorg. Chem.*, Vol. 38, 1432 (1999)), it is disclosed that Zr(OiPr)$_2$(dpm)$_2$ is a mixture and can be separated in Zr$_2$(OiPr)$_6$(dpm)$_2$ and Zr(dpm)$_4$ by a recrystallization.

Since Zr$_2$(OiPr)$_6$(dpm)$_2$ is a dimer, its molecular weight is high and, according to a pamphlet (*High Purity Precursors for Advanced Materials*, p.15 (1999)) of Inorgtech, England, its sublimation temperature is 250° C. at 0.1 Torr. It is true that the thermal decomposition temperatures of Zr(OiPr)$_2$(dpm)$_2$ and Zr$_2$(OiPr)$_6$(dpm)$_2$ become lower but it is not preferred that the necessary sublimation temperature becomes high as compared with monomers.

Further, Zr(dpm)$_4$ is soluble in THF at room temperature as good as 0.6 mol/liter but it is soluble in butyl acetate and in toluene to an extent of only about 0.2 mol/liter. Thus, there is a disadvantage that selection of the solvent is limited.

SUMMARY OF THE INVENTION

As a Zr compound for the formation of a PZT film using Pb(dpm)$_2$, the invention provides a compound having a low reactivity with Pb(dpm)$_2$, having a thermal decomposition temperature which is lower than Zr(dpm)$_4$ and similar to Pb(dpm)$_2$, showing a high sublimation pressure as a monomer and being well soluble in a solvent such as butyl acetate and toluene. The invention further provides a process for the manufacture of such a compound. The invention still further provides a liquid composition for the formation of a PZT film using the compound.

The Zr compound of the invention is a compound represented by the formula

Zr(OR)(L)$_3$                                   (formula I)

(in which R is an alkyl group having 1–5 carbon(s); and L is a β-diketonate group).

The Zr compound of the invention is zirconium isopropoxy tris(dipivaloylmethanate) Zr(OiPr)(dpm)$_3$ which is a compound of the formula I where R is isopropyl and L is dipivaloylmethanate.

A process for the manufacture of the Zr compound of the invention is a process where 1 mol of zirconium tetraalkoxide and 3 mol of a β-diketone are made to react in an organic solvent, the solvent is evaporated therefrom and the residue is purified by sublimation in vacuo.

A process for the manufacture of zirconium isopropoxy tris(dipivaloylmethanate) Zr(OiPr)(dpm)$_3$ of the invention is a process where 1 mol of zirconium tetraisopropoxide Zr(OiPr)$_4$ and 3 mol of dipivaloylmethane dpmH are made to react in an organic solvent, the solvent is evaporated therefrom and the residue is purified by sublimation in vacuo.

The liquid composition for the formation of a PZT film according to the invention is a composition where the zirconium compound of the invention, lead bis(β- diketonate) and titanium di(alkoxy)bis(β-diketonate) are dissolved in an organic solvent.

The liquid composition for the formation of a PZT film according to the invention is a composition where zirconium isopropoxy tris(dipivaloylmethanate) Zr(OiPr)(dpm)$_3$, lead bis(dipivaloylmethanate) Pb(dpm)$_2$ and titanium di(isopropoxy)bis(dipivaloylmethanate) Ti(OiPr)$_2$(dpm)$_2$ are dissolved in an organic solvent.

The organic solvent in the liquid composition for the formation of a PZT film according to the invention is one solvent selected from a group consisting of butyl acetate, n-butyl ether, toluene and THF.

DETAILED DESCRIPTION OF THE INVENTION

The Zr compound of the invention is a compound represented by the formula

Zr(OR)(L)$_3$    (formula I)

(in which R is an alkyl group having 1–5 carbon(s); and L is a β-diketonate).

To be more specific, R is a species selected from a group consisting of methyl, ethyl, isopropyl, tert-butyl, isobutyl, tert-amyl and neopentyl.

L is dipivaloylmethanate(=2,2,6,6-tetramethyl-3,5-heptanedionate), 2,6-dimethyl-3,5-heptanedionate, 2,2,6,6-tetramethyl-3,5-octanedionate, 2,2,6-trimethyl-3,5-heptanedionate, 6-ethyl-2,2-dimethyl-3,5-octanedionate or the like.

Among those compounds, the most easily manufactured Zr compound is zirconium isopropoxy tris (dipivaloylmethanate) Zr(OiPr)(dpm)$_3$. As hereunder, description will be given in detail by taking this compound as an example.

The process for the manufacture of zirconium isopropoxy tris(dipivaloylmethanate) Zr(OiPr)(dpm)$_3$ according to the invention is a method in which 1 mol of zirconium tetraisopropoxide Zr(OiPr)$_4$ and 3 mol of dipivaloylmethane dpmH are made to react in an organic solvent, then the solvent is evaporated therefrom and the residue is purified by sublimation in vacuo.

Zr(OiPr)$_4$ prepared by decomposition of the adduct followed by distilling is preferred since the reaction is apt to proceed easily and the impurities can be made small.

Examples of the organic solvent used for the reaction are toluene, hexane, heptane and octane. Reaction temperature is a boiling point thereof and the reaction is carried out in a refluxing state. Reaction time is 1 to 10 hour(s). After the reaction, the by-produced isopropanol and the solvent are evaporated under ordinary pressure and in vacuo. After that, the remaining residue in the reactor is finely ground, placed in a sublimation tube and the temperature is raised at 0.3 Torr whereupon a white sublimate is separated on the wall of the tube at near 190° C. This is Zr(OiPr)(dpm)$_3$ of the invention.

Result of identification and physical property of Zr(OiPr)(dpm)$_3$ obtained in Example 1 are as follows.

(1) Analysis of Composition

As a result of an ICP atomic emission spectrometry, analytical value of Zr was 13.4% by weight (theoretical value: 13.03% by weight).

(2) Analysis of Impurities

Result of an ICP atomic emission spectrometry (unit: ppm) is 2 for Al, 2 for Ca, 1 for Fe, 1 for Mg and 1 for Ti whereby the product was in high purity.

As a result of the total Cl analysis, Cl was 3 ppm.

(3) Molecular Weight

This was measured by a benzene cryoscopic method.

Sample: 0.8676 g; benzene: 20.5 g

ΔT=0.291° C., 0.301° C., 0.273° C. (0.288° C. in average)

Accordingly, molecular weight =752. Since the formula weight for Zr(OiPr)(dpm)$_3$=700.1, degree of association was 1.07.

(4) EI-MS

Conditions for the Measurement

Apparatus: JEOL AX505W

Ionizing method: EI

Temperature of ion source: 230° C.

Ionization energy: 70 eV

Figure 1:
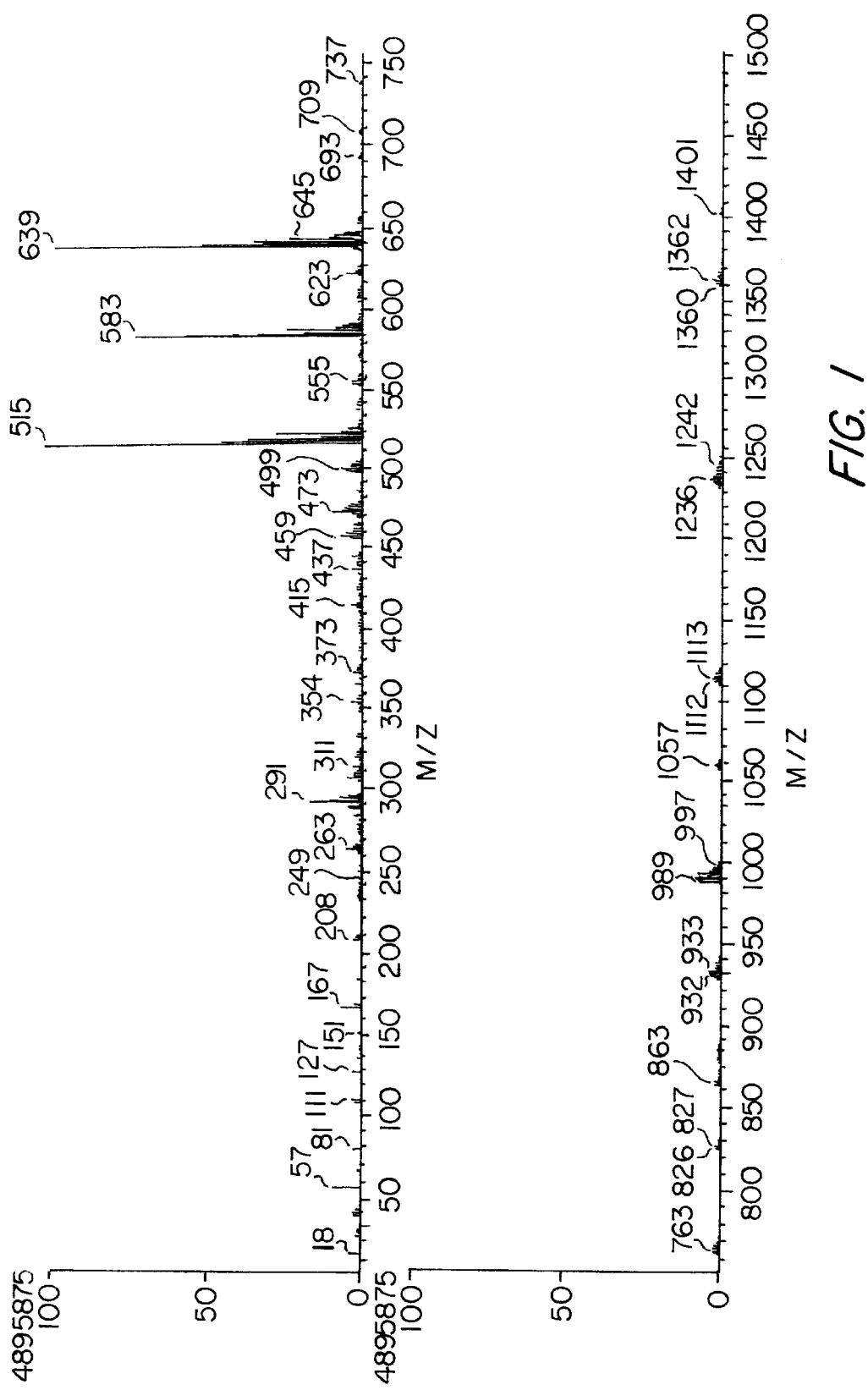
FIG. 1 is a graph showing the result of an ET-MS measurement for Zr(OiPr)(dpm)$_3$.

Result of the measurement is shown in FIG. 1.

There are five isotopes for Zr and, taking the fact that 51.46% is $^{90}$Zr, main m/z and intensity (%) together with ion species thereof are given below. Incidentally, there was no molecular ion Zr(OiPr)(dpm)$_3$$^+$(m/z=698).

m/z=639 (97%) Zr(dpm)$_3$$^+$ 583 (72%) Zr(dpm)$_2$((Me$_3$C)COCHC(H)O)$^+$ 515 (100%) Zr(OiPr)(dpm)$_2$$^+$ (5) $^1$H-NMR Conditions for the Measurement Apparatus: Bruker AC300P (300 MHz)

Solvent: benzene-d$_6$

Method: 1D

Figure 2:
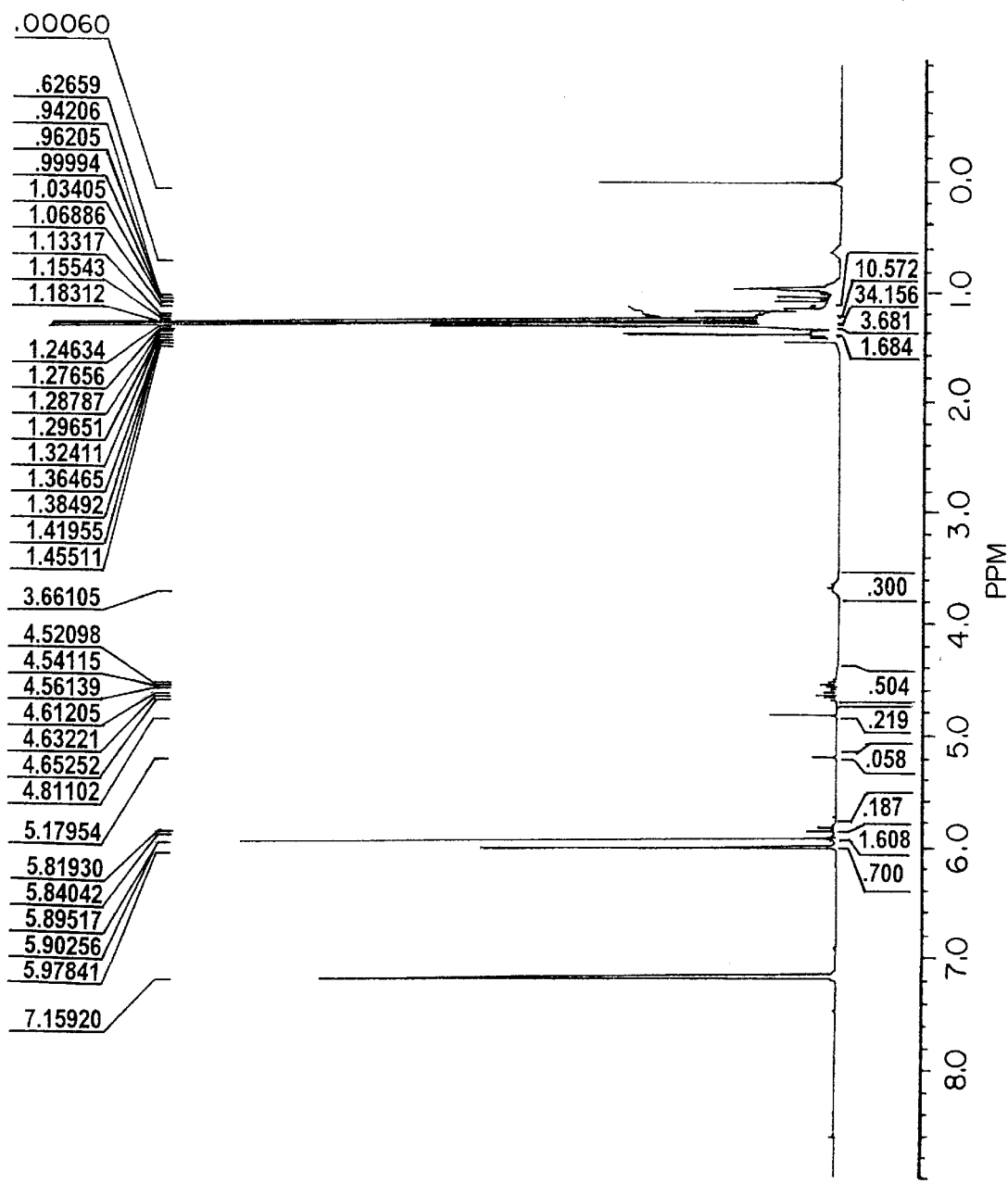
FIG. 2 is a graph showing the result of a $^1$H-NMR measurement for Zr(OiPr)(dpm)$_3$.

Result of the measurement is shown in FIG. 2.

δ$_H$ (ppm) and (assignment) are given below.

1.16+1.21+1.25 (54H, C(CH$_3$)$_3$)

1.29+1.36 (6H, OCH(CH$_3$)$_2$)

3.66+4.54+4.63+4.81+5.18 (1H, OCH(CH$_3$)$_2$)

5.84+5.90+5.98 (3H, CH)

(6) FT-IR

Conditions for the Measurement

Apparatus: Shimadzu FT-IR 8600

Method: A solution in toluene was cast on a KBr plate and then toluene was removed by evaporation.

Resolution: 4.0 cm$^{-1}$

Figure 3:
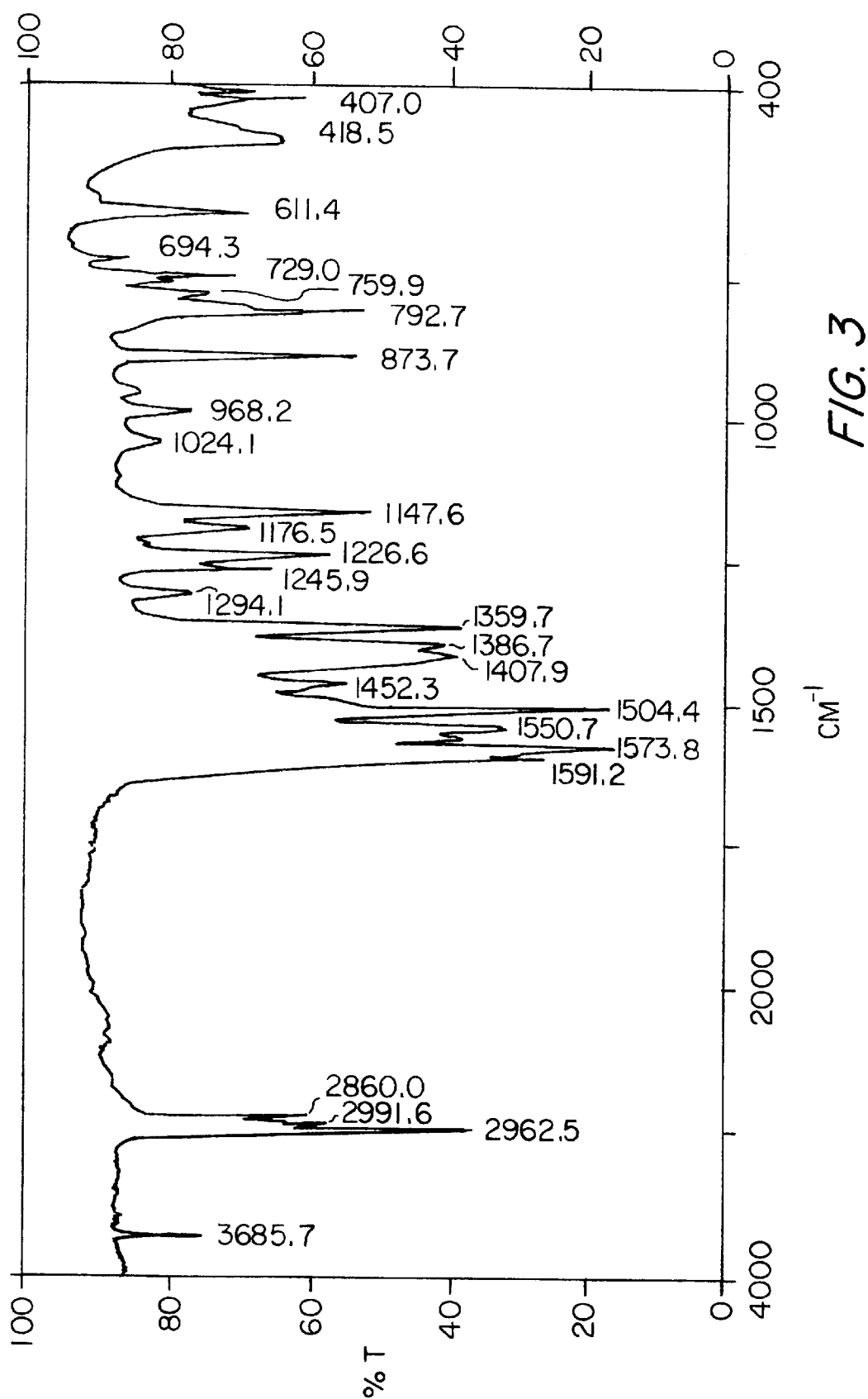
FIG. 3 is a graph showing the result of an FT-IR measurement for Zr(OiPr)(dpm)$_3$.

Result of the measurement is shown in FIG. 3.

Spectrum (cm$^{-1}$)

2963, 2904, 2866, 1591, 1574, 1551, 1504, 1452, 1408, 1387, 1360, 1294, 1245, 1227, 1177, 1148, 1024, 968, 874, 793, 760, 729, 694, 611, 419, 407

(7) Vapor Pressure

Measured value by a gas saturation method was 0.1 Torr/160° C.

(8) Physical Properties

White crystals having a melting point of 210° C. or higher (9) TG-DTA

Conditions for the Measurement

Sample weight: 15.9 mg

Figure 4:
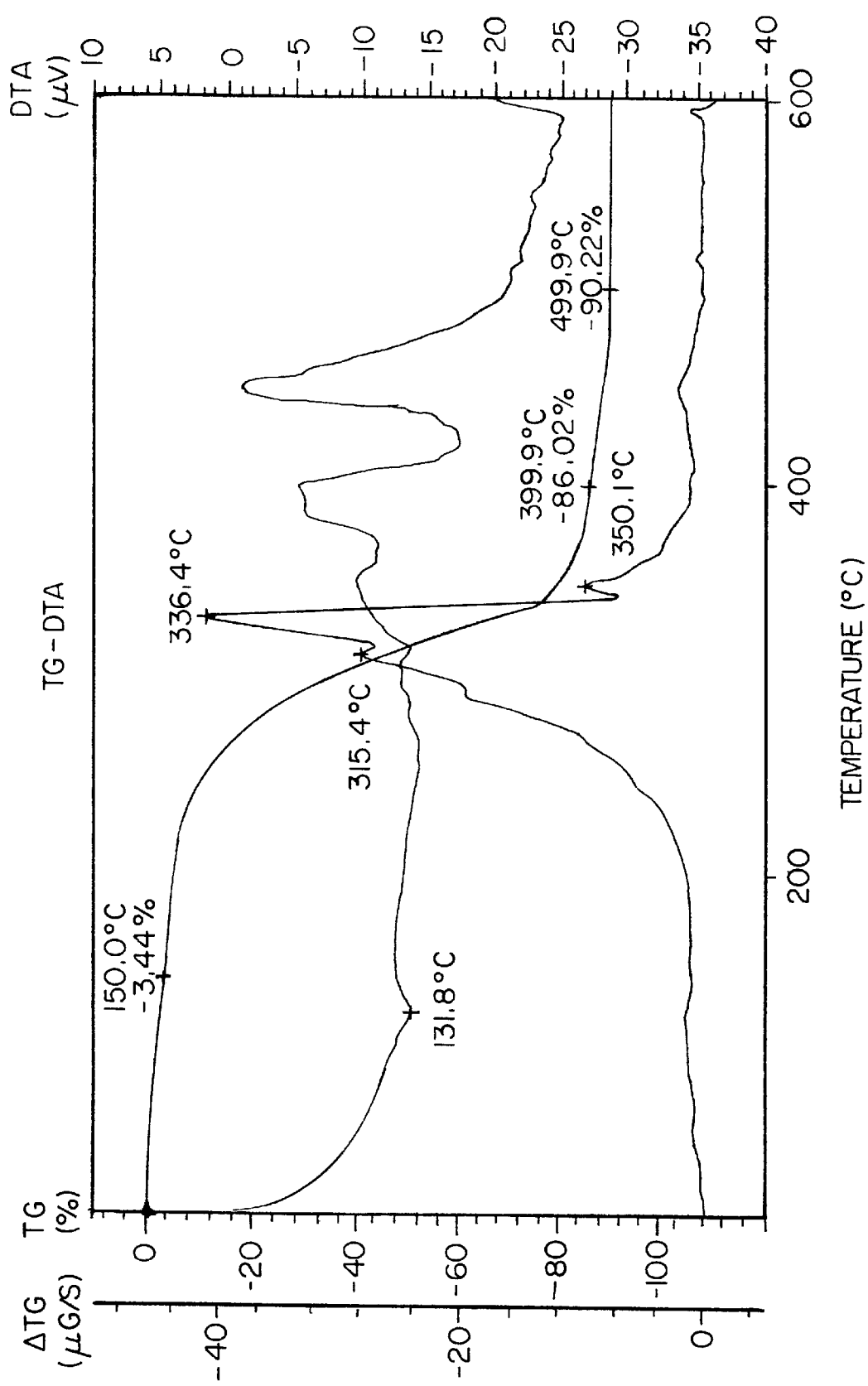
FIG. 4 is a graph showing the result of a TG-DTA measurement for Zr(OiPr)(dpm)$_3$.

Atmosphere: Ar of 1 atm
Temperature rising rate: 10.0 deg/min
Result of the measurement is shown in FIG. 4.

The reason why about 3% of weight reduction was noted until 150° C. is presumed to be the fact that, during the sample was set in a measuring system, it reacted with moisture in the air and the alcohol formed by hydrolysis is evaporated.

(10) Solubility

The amount (grams) dissolved in 1 liter of the solvent at room temperature is shown in Table 1.

For comparison, the data for $Zr(dpm)_4$ are shown in the lower line.

It is clear from Table 1 that $Zr(OiPr)(dpm)_3$ is more soluble than $Zr(dpm)_4$ to an extent of 2- to 4-fold in the solvents other than THF.

TABLE 1

| Solvent Species | THF | Toluene | Hexane | Butyl Acetate | n-Butyl Ether |
|---|---|---|---|---|---|
| $Zr(OiPr)(dpm)_3$ | 980 | 1100 | 620 | 460 | 430 |
| $Zr(dpm)_4$ | 1020 | 290 | 430 | 180 | 240 |

As a result of a total judgement mainly from the composition analysis, EI-MS, $^1$H-NMR and FT-IR, this compound was identified as $Zr(OiPr)(dpm)_3$.

As will be noted from the description for its nature, this $Zr(OiPr)(dpm)_3$ is a monomer, has a high vapor pressure as compared with $Zr_2(OiPr)_6(dpm)_2$ and is well soluble in various solvents as compared with $Zr(dpm)_4$.

Now, the lowest substrate temperature where $ZrO_2$ film deposited from $Zr(OiPr)(dpm)_3$ of this invention onto a substrate by a CVD was investigated (Example 2) and was found to be about 400° C. This temperature was about 50° C. lower as compared with 450° C. of $Zr(dpm)_4$ (Comparative Example 1). This is because an OiPr group which is present only one therein starts in decomposition at a relatively low temperature. That can be estimated from the TG-DTA as well. As such, $Zr(OiPr)(dpm)_3$ starts in the thermal decomposition at low temperature and, therefore it is convenient for the formation of a PZT film at low temperature.

Examples of a β-diketonate in lead bis(β-diketonate) which is a component of a liquid composition for the formation of a PZT film of the invention are dipivaloylmethanate(=2,2,6,6-tetramethyl-3,5-heptanedionate), 2,6-dimethyl-3,5-heptanedionate, 2,2,6,6-tetramethyl-3,5-octanedionate, 2,2,6-trimethyl-3,5-heptanedionate and 6-ethyl-2,2-dimethyl-3,5-octanedionate.

Examples of an alkoxy group in titanium di(alkoxy) bis(β-diketonate) which is a component of a liquid composition for the formation of a PZT film of the invention are methoxy, ethoxy, isopropoxy, tert-butoxy, isobutoxy, tert-amyloxy and neopentoxy while examples of a β-diketonate therein are dipivaloylmethanate (=2,2,6,6-tetramethyl-3,5-heptanedionate), 2,6-dimethyl-3,5-heptanedionate, 2,2,6,6-tetramethyl-3,5-octanedionate, 2,2,6-trimethyl-3,5-heptanedionate and 6-ethyl-2,2-dimethyl-3,5-octanedionate.

With regard to preferred components for a liquid composition for the formation of a PZT film of the invention, it is desirable that an alkoxy group and a β-diketonate are in the same species. Accordingly, the preferred composition is a combination of zirconium isopropoxy tris (dipivaloylmethanate), lead bis(dipivaloylmethanate) and titanium di(isopropoxy)bis(dipivaloylmethanate).

It is necessary that ratio of Pb:Zr:Ti of this composition and concentration thereof are appropriately determined depending upon the aimed component composition, substrate temperature and a CVD apparatus. This is because the ways of incorporation of the three elements into the film are affected each other depending upon the condition. It is shown in Example 4 that, when the composition of the invention is used, a PZT film can be formed by an ordinary thermal CVD apparatus.

The liquid composition for the formation of a PZT film according to the invention has a long pot life. As mentioned in Example 3 and Comparative Example 2, a combination of $Pb(dpm)_2$, $T(OiPr)_2(dpm)_2$ and $Zr(OiPr)(dpm)_3$ is stable for a long period at high concentrations as compared with a combination of $Pb(dpm)_2$, $Ti(OiPr)_2(dpm)_2$ and $Zr(dpm)_4$. One of the reasons therefor will be that $Zr(OiPr)(dpm)_3$ does not react with other components and, in addition, its solubility is 2- to 4-fold higher than $Zr(dpm)_4$. That is significantly noted when the solvent is not THF but is butyl acetate, n-butyl ether or toluene. The liquid composition for the formation of a PZT film according to the invention has a pot life of at least three months.

EXAMPLE 1

Manufacture of Zirconium Isopropoxy tris (dipivaloylmethanate); $Zr(OiPr)(dpm)_3$ A 500-ml four-necked flask equipped with a reflux condenser, a thermometer and stirring blades was made in vacuo followed by substituting with argon, 200 ml of toluene were charged and then 25.7 g (78.5 mmol) of $Zr(OiPr)_4$ and 43.5 g (236 mmol) of dipivaloylmethane dpmH were charged. After that, temperature was raised with stirring and the reaction was carried out by heating with refluxing for 7 hours. Then the solvent and by-produced isopropanol were evaporated in vacuo and, finally, the bath temperature was raised to 160° C. so that volatile substances in the flask were removed. The solid in the flask was taken out, finely pulverized and placed in a sublimation tube. This was made in vacuo 0.3 Torr and heated with a bath temperature of around 210° C. whereupon most of the content was sublimated and separated onto the wall of the tube. The white solid in an amount of 42.7 g was gained. As a result of identification, it was found to be $Zr(OiPr)(dpm)_3$ (61 mmol) and the yield was 78%.

EXAMPLE 2

Film Formation of $ZrO_2$ from $Zr(OiPr)(dpm)_3$ by CVD

A solution (concentration: 0.1 mol/liter) of $Zr(OiPr)(dpm)_3$ in butyl acetate was sent into a flash evaporator of 220° C. at the rate of 0.1 ml/minute, evaporated together with 0.3 slm of pre-heated argon gas and sent to a CVD chamber. This was mixed with 0.1 slm of pre-heated oxygen gas at the inlet of the CVD chamber, introduced onto an Si(100) substrate which was heated at 350° C. to 500° C. with a chamber pressure of 10 Torr and was thermally decomposed and deposited. After 20 minutes, the substrate was taken out and the film thickness was measured whereupon a $ZrO_2$ film of about 30 nm was found to be formed at 400° C. When the temperature was 450° C. or 500° C., it was about 50 nm.

Comparative Example 1

Film Formation of $ZrO_2$ by CVD of $Zr(dpm)_4$

The same operation as in Example 2 was carried out except that $Zr(dpm)_4$ was substituted for $Zr(OiPr)(dpm)_3$ in Example 2. At 400° C., film was almost nil and at 450° C., a $ZrO_2$ film of about 20 nm was formed which grew to about 40 nm at 500° C.

From the result of Example 2 and Comparative Example 1, it is noted that the lowest temperature of $Zr(OiPr)(dpm)_3$ for the formation of $ZrO_2$ film is about 50° C. lower than that of $Zr(dpm)_4$.

Example 3

Manufacture of a Liquid Composition for the Formation of a PZT Film and Measurement of its Pot Life n-Butyl acetate (285 ml) which was dehydrated to an extent of water content of not more than 20 ppm and deoxidized in vacuo was placed in a graduated flask, 17.2 g (30 mmol) of $Pb(dpm)_2$, 10.5 g (15 mmol) of $Zr(OiPr)(dpm)_3$ and 8.0 g (15 mmol) of $Ti(OiPr)_2(dpm)_2$ were dissolved therein and the gaseous part was changed to dry nitrogen followed by sealing tightly. The solution was transparent and was not turbid at all. Concentrations were 0.1 mol/liter of Pb, 0.05 mol/liter of Zr and 0.05 mol/liter of Ti. This solution was kept at room temperature and, after 1 month and 3 months, observations were carried out for deterioration, coloration and production of precipitate. Even after 3 months, there was no change at all but the solution was transparent.

The solution (50 ml) after 3 months was taken in a flask, the solvent was evaporated at room temperature in vacuo and then $Pb(dpm)_2$, $Zr(OiPr)(dpm)_3$ and $Ti(OiPr)_2(dpm)_2$ were evaporated and recovered (6.2 g) in vacuo (0.03 Torr) by raising the temperature of the heating bath to 120° C. to 200° C. When the composition of the recovered substance was analyzed, Pb:Zr:Ti was found to be 1.06:0.49:0.51. In the flask, 0.2 g of a residue after the evaporation was present and, when calculated therefrom, 97% of the components of Pb, Zr and Ti were evaporated. In the inner wall, the solid was adhered only a little and it is estimated that substantially all of them were evaporated. There will be no possibility of change to a compound having an increased molecular weight and a reduced vapor pressure due to a ligand exchange and a polymerization.

Comparative Example 2

Manufacture of a Liquid Composition for the Formation of a PZT Film Using $Zr(dpm)_4$ and Measurement of its Pot Life The same operation as in Example 3 was carried out except that 12.4 g (15 mmol) of $Zr(dpm)_4$ was substituted for 10.5 g (15 mmol) of $Zr(OiPr)(dpm)_3$ in Example 3 to prepare a solution. The content was almost dissolved although a turbidity in white color was noted a little. After 3 days, a few amount of white sediment was noted on the bottom and the solution became transparent. The solution was filtered through a filter and tightly closed in a flask. After 1 month, a white solid was separated on the bottom of the flask. From this result, it is estimated that, in the case of co-existence of three components, solubility of $Zr(dpm)_4$ was considerably low.

Example 4

Film Formation of PZT by a Liquid Composition for the formation of a PZT film using $Zr(OiPr)(dpm)_3$ $Pb(dpm)_2$, $Zr(OiPr)(dpm)_3$ and $Ti(OiPr)_2(dpm)_2$ were dissolved in a deoxidized n-butyl acetate to make their concentrations 0.1 mol/liter of Pb, 0.04 mol/liter of Zr and 0.04 mol/liter of Ti. This solution was sent to a flash evaporator of 220° C. at the rate of 0.1 ml/minute, evaporated together with 0.3 slm of a pre-heated argon gas and sent to a CVD chamber. This was mixed with 0.7 slm of pre-heated oxygen gas at an inlet of the CVD chamber, introduced onto an $Pt(111)/SiO_2/Si$ substrate which was heated at 550° C. with a chamber pressure of 10 Torr and was thermally decomposed and deposited. After 30 minutes, the substrate was taken out and the film thickness was measured whereupon a film of 150 nm was found to be formed. From an XRD, this film was a PZT of a perovskite phase. When this film was dissolved and analyzed for its composition, Pb:Zr:Ti was found to be 1.02:0.45:0.55.

When $Zr(OiPr)(dpm)_3$ of the invention is used for the preparation of an n-butyl acetate solution containing all three components for the formation of a PZT film by a solution flash CVD, a solution of a high concentration having a long pot life is prepared. Since the three components can be made into a single solution, control of the composition is easy and that is effective for a large-scale production of a PZT film. In addition, a $ZrO_2$ film can be formed at lower temperature than in the case of $Zr(dpm)_4$.

What is claimed is:

1. The compound zirconium isopropoxy tris(dispivaloymehtanate).

2. A process for the manufacture of zirconium isopropoxy tris(dipivaloylmethanate), wherein 1 mol of zirconium tetraisopropoxide and 3 mol of dipivaloylmethane are made to react in an organic solvent and then the solvent is evaporated therefrom followed by purifying by sublimation in vacuo.

3. A liquid composition for the formation of a PZT film, wherein zirconium isopropoxy tris(dipivaloylmethanate), lead bis(β-diketonate) and titanium di(alkoxy)bis(β-diketonate) are dissolved in an organic solvent.

4. A liquid composition for the formation of a PZT film, wherein zirconium isopropoxy tris(dipivaloylmethanate), lead bis(dipivaloylmethanate) and titanium di(isopropoxy)bis(dipivaloylmethanate) are dissolved in an organic solvent.

5. The liquid composition for the formation of a PZT film according to claim 4, wherein the organic solvent is a species selected from a group consisting of butyl acetate, n-butyl ether, toluene and THF.

* * * * *